(12) United States Patent
Stoffella

(10) Patent No.: US 6,203,545 B1
(45) Date of Patent: Mar. 20, 2001

(54) IMPLANT FOR FIXING BONE FRAGMENTS AFTER AN OSTEOTOMY

(75) Inventor: Rudolf Stoffella, Vienna (AU)

(73) Assignee: Waldemar Link (GmbH & Co.), Hamburg (DE)

( * ) Notice: Subject to any disclaimer, the term of this patent is extended or adjusted under 35 U.S.C. 154(b) by 0 days.

(21) Appl. No.: 09/155,524

(22) PCT Filed: Mar. 21, 1997

(86) PCT No.: PCT/EP97/01452

§ 371 Date: Mar. 4, 1999

§ 102(e) Date: Mar. 4, 1999

(87) PCT Pub. No.: WO97/35528

PCT Pub. Date: Oct. 20, 1997

(30) Foreign Application Priority Data

Mar. 26, 1996 (AT) .......................................... 167/96

(51) Int. Cl.$^7$ ................................................ A61B 17/56
(52) U.S. Cl. ................................................................ 606/74
(58) Field of Search ................................ 623/59, 60, 62, 623/63, 67, 74, 75, 16.11, 13.14

(56) References Cited

U.S. PATENT DOCUMENTS 5,374,268 * 12/1994 Sander ................................ 606/72
5,571,103 * 11/1996 Bailey ................................. 606/62
5,697,934 * 12/1997 Huebner ............................ 606/103

FOREIGN PATENT DOCUMENTS

261038 * 3/1988 (EP) .
401650 * 12/1990 (EP) .
646353 * 4/1995 (EP) .
2722545 * 3/1993 (FR) .

* cited by examiner

Primary Examiner—Bruce Snow
(74) Attorney, Agent, or Firm—Morrison & Foerster LLP

(57) ABSTRACT

An implant for fixing bone fragments after an osteotomy, especially for treating the misalignments of a metatarasal bone, includes a clasp with two arms and a screw. The arms are connected to each other at one end so that they form a screw eyelet adapted to receive the screw. The arms are configured to be introduced into the medullary cavity of a first bone fragment, and the screw is configured to be inserted a second bone fragment. The clasp is made of an elastic material, so that in a relaxed state the distance between the arms increases toward their free ends. The clasp is configured for being introduced into the medullary cavity of the bone fragment in a compressed state, so that after insertion the arms spread open and secure the clasp in that bone fragment.

14 Claims, 1 Drawing Sheet

IMPLANT FOR FIXING BONE FRAGMENTS AFTER AN OSTEOTOMY

BACKGROUND OF THE INVENTION

The invention relates to an implant for fixing an osteotomy, in particular for treating an axial deviation of a metatarsal bone, e.g. hallux valgus, and consisting of a clasp with two arms which are connected to each other at one of their ends.

Osteotomies for treating hallux valgus have already been known for decades and have the object of anatomically reconstructing the axis of the 1st metatarsal. It is necessary in this context, after repositioning the osteotomy, to fix the two bone fragments in their repositioned state in order to prevent mobility between the fragments and to permit primary bone healing without callus forming as a result of movement. There are various techniques for this fixing.

Thus, it is already known to connect the two bone fragments to each other by means of a screw which is introduced into a pre-drilled slide hole in the proximal fragment and is screwed into a threaded hole in the distal fragment. It is also already known to use self-tapping screws or hollow screws which permit a temporary fixation of the osteotomy by means of Kirschner wires belonging to the system. The use of these screws causes substantial inter-fragment compression, but this has not proven to be of any advantage since a pressure of more than 200 KTa (30 psi) leads to necrosis of the cortical bone.

It has already been proposed to fix an osteotomy by means of a wire which is pushed through pre-drilled holes in the osteotomy, whereupon the wire ends are twisted and the twisted area is embedded in a separate hole in the bone. This type of fixing is involved and time-consuming.

Fixing the osteotomy with a drill wire protruding from the skin causes temporary immobilization of the basal joint of the big toe, which is a disadvantage.

Bone clamps are also known for fixing the osteotomy, but their use involves the risk of splintering of the bone.

Also used for fixing the osteotomy are plates which have to be secured to the cortical bone via a number of screws, with the result that more bone mass is lost, and considerable surgical outlay is necessary for this.

An osteosynthesis clasp is known (FR-A-2722545) which consists of two parallel arms which are connected to each other in a U shape via a single arch without reverse point. One bone fragment is gripped using the arch of the clasp, and the free ends of the arms are inserted into the other fragment, where they are intended to be maintained by virtue of their undulation, but this is not sufficiently reliable.

Starting from the last-mentioned prior art, the object of the invention is to make available a clasp for fixing an osteotomy in accordance with the preamble of claim 1, which clasp is particularly suitable for treating an axial deviation of a metatarsal bone and ensures a sufficiently stable fixing of the osteotomy, can be fitted easily and without irritations, can be anchored in the bone and can also be removed again in a manner which is well tolerated by the patient.

The solution according to the invention lies in the features of claim 1. According to the latter, the two arms, in the area of their ends connected to each other, delimit an eyelet for the passage of a screw which can be anchored in one of the two bone fragments. The other, free ends of the arms can spread open in the medullary cavity of the other bone fragment. This spreading of the arms in the medullary cavity of the bone is achieved by the fact that the distance between the two arms made of a flexible elastic material, for example steel wire, increases, at least in the unloaded, relaxed state, from the connection point in the direction towards their free ends. Upon introduction of the arms into the medullary cavity, they are pressed together and then, as a result of their flexible elastic properties, brace themselves on the wall of the medullary cavity when the pressure exerted on the arms ceases.

After osteotomy has been performed, the clasp is introduced proximally into the medullary cavity via the free ends of its two arms and braces itself there in the medullary cavity of the one bone fragment, after which the end of the clasp provided with the opening is anchored on the other bone fragment by means of the screw. Through this intramedullary anchoring of the clasp by means of the spread-out ends of the arms, on the one hand, and the screwing-tight of the clasp, on the other hand, the osteotomy acquires a sufficiently stable fixing and permits immediate loading and early mobilization with a hallux mobility splint. Costly wound care and restraint dressings which limit mobility are no longer necessary.

From the fourth week after the operation, the clasp and the screw can be removed using a stab incision, which procedure is well tolerated by the patient.

The screw eyelet is expediently designed as an eyelet with a contour essentially in the shape of an arc of a circle, and dimensioned so that the screw can be passed through this opening, but so that an undesired lateral movement of the screw inside the opening is nevertheless prevented, and the screw head exerts contact pressure on the bone fragment.

It is also of advantage if those ends of the two arms connected to each other and delimiting the opening are bent outwards from the arm plane set by the remaining part of the arms and lie in a plane approximately parallel to this arm plane. The distance between these two planes takes account of the lateral offset of the bone fragments.

The intramedullary anchoring can be improved by the fact that according to the invention the two arms have an undulation, preferably running in the arm plane.

However, the clasp can also be made of a memory metal, preferably a nickel/titanium alloy. Such memory metals are known and are also used for implants. These memory metals have a property which is such that in the event of mechanical deformation, they retain their shape effected by this mechanical deformation below certain temperatures, but return to their original shape when the temperature rises. Thus, if the clasp is made of a memory metal, the two ends of the arms can be brought towards each other after cooling the clasp, for example by spraying it with a cooling gas, and they initially maintain this shape. After the arms have been introduced into the medullary cavity, the temperature of the clasp rises to body temperature, whereupon the clasp made of memory metal again assumes its original shape, with the ends of the arms spread apart, and is thus braced on the wall of the medullary cavity.

BRIEF DESCRIPTION OF THE DRAWINGS

The invention is shown diagrammatically in the drawing, on the basis of an illustrative embodiment.

DETAILED DESCRIPTION OF THE PREFERRED EMBODIMENT

Figure 1:
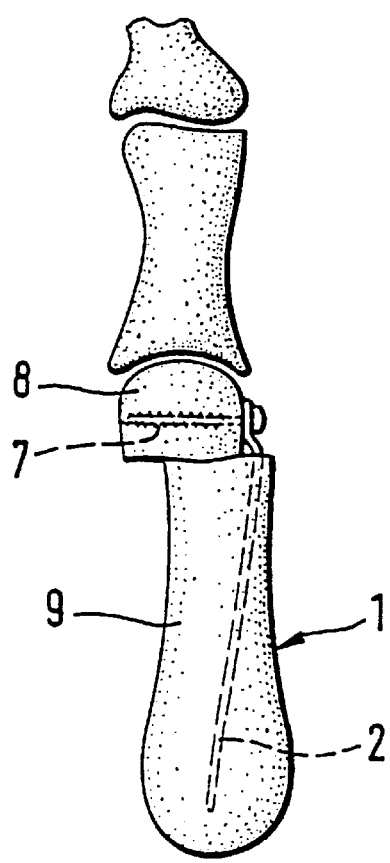
FIG. 1 shows the use of the implant according to the invention in the reconstruction of a hallux valgus.

FIG. 1 shows a metatarsal bone 1 following osteotomy and repositioning. To fix it, an implant is used which, in accordance with the invention, consists of a clasp 2 represented in FIGS. 2 and 3. This clasp 2 has two arms 3 which are connected to each other via one of their ends at 4 and there delimit an opening 6 formed by an eyelet 5, through which opening 6 a small-fragment screw 7 (see FIG. 1) can be passed, which screw is anchored in the usual way in the bone fragment 8.

Figure 2:
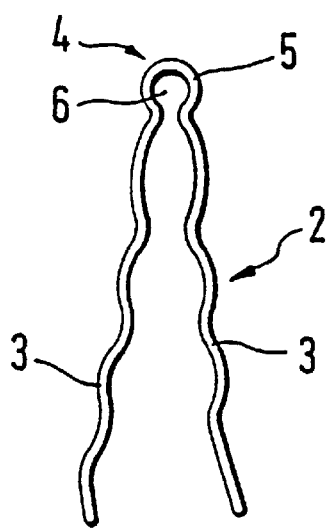
FIG. 2 represents the implant according to the invention in a plan view.

The two arms 3 of the clasp 2 are introduced into the medullary cavity of the bone fragment 9 and there assume their spread-out position represented in FIG. 2, as a result of which the clasp 2 is anchored in this medullary cavity. The anchoring is assisted by an undulation preferably running in the plane of the arm.

Figure 3:
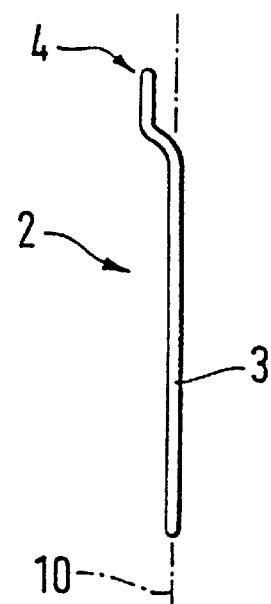
FIG. 3 represents it in a side view.

As is evident from FIGS. 1 and 3, those ends of the two arms connected to each other at 4 and delimiting the opening 6 are bent outwards from the plane 10 set by the remaining part of the arms 3 and they lie in a plane parallel to this arm plane 10. The lateral offset of the two bone fragments 8, 9 is accounted for in this way. The distance between these planes is therefore adapted to this lateral offset.

The clasp 2 can be made of a flexible elastic steel wire, in which case the distance between the two arms 3 in the unloaded state increases from the connection point 4 in the direction towards the free ends of the arms. Upon introduction of the arms 3 into the medullary cavity, these arms are pressed together and brace themselves in the medullary cavity when the pressure exerted manually on the arms ceases. However, the clasp 2 can also be made of a memory metal, preferably a nickel/titanium alloy, in other words a metal which as a result of the crystalline structure of the alloy in the austenitic phase retains the mechanically generated deformation at low temperatures, but returns to its original shape when heated, as a result of the memory property. In the present case, the original shape is represented in FIG. 2. When cooled, however, for example by means of a cooling gas being sprayed on, the arms can be brought mechanically into an approximately parallel configuration and they can retain this configuration during introduction into the medullary cavity, as a result of which this introduction is made easier. As the clasp is warmed by the body temperature, so the arms return to their original shape represented in FIG. 2 and are braced in the medullary cavity. This procedure thus facilitates the introduction of the arms 3 of the clasp 2 into the medullary cavity.

What is claimed is:

1. An implant for fixing an osteotomy, comprising a clasp having two arms and formed of an elastic material and a screw, each arm having a free end and a connected end connected to the connected end of the other arm, a distance between the two arms when said clasp is in a relaxed state increases from the connected ends of the two arm toward their free ends, and wherein the two arms are configured for introduction into a medullary cavity of a first bone fragment and to form a screw eyelet adapted to receive the screw, the screw being configured for insertion into a second bone fragment, wherein the clasp being configured so that the free ends of the arms are introduced into the medullary cavity in a compressed state.

2. The implant of claim 1, wherein said screw eyelet is formed with a contour essentially in the shape of an arc of a circle.

3. The implant of claim 1, wherein said free ends of the arms form an arm plane and said connected ends lie in another plane which is approximately parallel to the arm plane.

4. The implant of claim 1, wherein the arms have undulations formed therein.

5. The implant of claim 4, wherein the undulations of the arms lie in an arm plane formed by the free ends of the arms.

6. The implant of claim 1, wherein said clasp is made of a shape memory metal.

7. The implant of claim 6, wherein said shape memory metal is a nickel/titanium alloy.

8. An implant for fixing an axial deviation of an metatarsal bone, comprising a clasp with two arms formed of an elastic material and a screw, each arm having a free end and a connected end connected to the connected end of the other arm, a distance between the two arms when said clasp is in a relaxed state increasing from the connected ends of the two arm toward their free ends, wherein the two arms are configured for introduction into a medullary cavity of a first bone fragment and to form a screw eyelet adapted to receive the screw, the screw being configured for insertion into a second bone fragment, the clasp being configured so that the free ends of the two arms are introduced into the medullary cavity in a compressed state.

9. The implant of claim 8, wherein said screw eyelet is formed with a contour essentially in the shape of an arc of a circle.

10. The implant of claim 8, wherein said free ends of the arms form an arm plane and said connected ends lie in another plane approximately parallel to the arm plane.

11. The implant of claim 8, wherein the arms have undulations formed therein.

12. The implant of claim 11, wherein the undulations of the arms lie in an arm plane formed by the free ends of the arms.

13. The implant of claim 8, wherein said clasp is made of a shape memory metal.

14. The implant of claim 13, wherein said shape memory metal is a nickel/titanium alloy.

* * * * *